United States Patent
Knauss

(10) Patent No.: US 7,316,795 B1
(45) Date of Patent: Jan. 8, 2008

(54) METHOD FOR OVERMOLDING A PAINTED SILICONE RUBBER HUMAN EXTREMITY PROSTHESIS

(76) Inventor: Stefan Johannes Knauss, 2123 Brigden Rd., Pasadena, CA (US) 91104

( * ) Notice: Subject to any disclaimer, the term of this patent is extended or adjusted under 35 U.S.C. 154(b) by 312 days.

(21) Appl. No.: 10/792,548

(22) Filed: Mar. 2, 2004

(51) Int. Cl.
  B29C 63/22 (2006.01)
  B29C 35/02 (2006.01)
  A61L 27/60 (2006.01)
  A61F 2/60 (2006.01)
  A61F 2/54 (2006.01)

(52) U.S. Cl. .................. 264/313; 264/279; 264/135
(58) Field of Classification Search ............. 62/53; 427/2.1; 264/279, 313
  See application file for complete search history.

(56) References Cited

U.S. PATENT DOCUMENTS

| | | | | |
|---|---|---|---|---|
| 2,453,604 | A * | 11/1948 | Tenebaum et al. | 264/222 |
| 3,400,408 | A * | 9/1968 | Garcia | 623/43 |
| 3,789,518 | A * | 2/1974 | Chase | 434/272 |
| 3,905,376 | A * | 9/1975 | Johnson et al. | 36/154 |
| 4,472,226 | A * | 9/1984 | Redinger et al. | 156/242 |
| 4,735,754 | A * | 4/1988 | Buckner | 264/40.1 |
| 4,778,467 | A * | 10/1988 | Stensaas et al. | 623/23.64 |
| 4,871,502 | A * | 10/1989 | LeBisch et al. | 264/222 |
| 5,008,058 | A * | 4/1991 | Henneberger et al. | 264/134 |
| 5,014,361 | A * | 5/1991 | Gray | 2/67 |
| 5,088,125 | A * | 2/1992 | Ansell et al. | 2/167 |
| 5,888,231 | A * | 3/1999 | Sandvig et al. | 623/36 |
| 5,980,576 | A * | 11/1999 | Graf et al. | 623/33 |
| 6,153,139 | A * | 11/2000 | Marquette | 264/219 |
| 6,818,164 | B1 * | 11/2004 | Cooper et al. | 264/73 |
| 6,852,269 | B2 * | 2/2005 | Eberle et al. | 264/512 |

FOREIGN PATENT DOCUMENTS

| | | | |
|---|---|---|---|
| GB | 2 067 074 | * | 7/1981 |
| GB | 2 243 324 | * | 10/1981 |

* cited by examiner

Primary Examiner—Christina Johnson
Assistant Examiner—Matthew J. Daniels
(74) Attorney, Agent, or Firm—Frederick Gotha

(57) ABSTRACT

The invention relates to method for overmolding a painted silicone prosthesis of a human extremity. A silicone prosthesis is first molded from a solid replica of a human extremity and then painted to closely resemble the color of the recipient person. An elasotmeric polymer material having the properties of elasticity, transparency, and non-adhesiveness to cured silicone rubber is applied to the replica to form a transparent glove-like overmold. The glove has an inner surface that is mirrored by the surface of the replica. The distal portion of the glove-like overmold is partially filled with a predetermined amount of viscous uncured silicone liquid and the painted silicone prosthesis is then inserted into the glove which is stretched tightly over the prosthesis. A compressive force is externally applied in a radial compressive and proximate direction to uniformly distribute the liquid silicone over the painted surface of the prosthesis. The silicone is allowed to cure and bonds to the surface of the prosthesis but does not adhere to the transparent glove-like overmold.

19 Claims, 5 Drawing Sheets

METHOD FOR OVERMOLDING A PAINTED SILICONE RUBBER HUMAN EXTREMITY PROSTHESIS

FIELD OF THE INVENTION

This invention relates to a method of applying a thin layer or film of uncured silicone rubber to the painted surface of a silicone rubber human extremity prosthesis.

BACKGROUND

Creating an aesthetic silicone rubber prosthesis of a human extremity traditionally involved producing a mold of the extremity, painting the extremity prosthesis made from the mold to closely resemble the color of the human extremity, and then applying a protective coating over the painted surface of the extremity to protect against abrasions and ordinary wear.

There are several methods used in the prior art to produce the mold from which the silicone prosthesis is made and these methods are well known in the prior art. One such method is the use of a multi-piece mold which may be solid or flexible but typically produces an unsightly seam at the location where the pieces are merged together to form the prosthesis.

Another method is slurry molding whereby the mold is created by electroplating over a wax model of the human extremity. In this process, metal is deposited on the wax model to form the mold; the wax is then removed and a silicone slurry, rubber, is poured into the mold which is then subjected to a rotational molding process. Curing is achieved either by the application of heat or by the combination of heat and the passage of time. Slurry molding has the advantage of producing a silicone rubber prosthesis that does not contain a seam. However, because of the difficulty in painting the interior of the prosthesis, the use of this method is expensive and time consuming and thus a chief drawback in using this process.

And in yet another method to produce a prosthesis, silicone sheets are sculptured directly, without using molds, to form the prosthesis. This process is described in an article entitled "A Silicone Elastomer Manipulation Technique for the Production of Medical Devices" by Jan DeCubber in the *Journal of Facial and Somato Prosthesis*.

In the method above referred to as a multi-piece molding process, the prosthesis would be painted to closely resemble the color of the person for whom the prosthesis has been made by either colors to the inside of the mold before filling the mold or by painting the monochromatic casting. All the prostheses produced from the molding processes above described are painted to resemble the color of the person and may rely to varying degrees upon intrinsic or extrinsically painted colorants. A heavy coating of clear silicone is then sprayed or hand-painted over the entire prosthesis as a protective layer over the colored surface. The purpose of the coating is to protect the colored surface against abrasive exposures during ordinary use that would scrape the surface and thus detract from an aesthetic and realistic appearance of the prosthesis. However, the application of the coating as performed or done in the prior art creates a surface that lacks the desired level of surface detail as that of human skin and consequently diminishes from the aesthetic and realistic appearance of the extremity.

SUMMARY OF THE INVENTION

The present invention relates to creating a protective cover surface for a painted prosthesis that preserves the detail of the human skin by an overmolding method of a painted silicone rubber prosthesis; preserving the detail is achieved through the use of a transparent glove-like mold made of an elastomeric polymer material. The glove-like mold is produced by applying an elastomeric polymer coating material to a solid replica of the human extremity; this replica is also used to produce the mold of the monochromatic silicone extremity prosthesis. The elastomeric polymer coating material that is used has the properties of transparency, extensive elasticity, and of being non-adhesive to cured silicone rubber.

The method of this invention is for overmolding the painted surface of a monochromatic silicone prosthesis of a human extremity. The method may be used for extremities such as the human hand or foot. In the human hand prosthesis method embodiment, the surface features duplicating the human hand of the prosthesis recipient that appear on the silicone hand prosthesis are molded from a solid replica; the replica has the identical surface features as the recipient's hand. In performing the method of this invention to overmold a human extremity, an elastomeric polymer material having the property of being transparent, elastic, and non-adhesive to cured silicone rubber, is applied to the surface of the replica to form a transparent glove-like mold of uniform thickness. The elastomeric polymer material is preferably a thermoplastic elastomer, but alternatively may also be made of any other strong stretchable and formable material, e.g., a polyurethane elastomer. The elastomeric polymer material may be applied repeatedly by dipping the replica into the material to form a coating of a predetermined or desired thickness. The material may also be applied to the replica by spraying or by brushing the material over the surface of the replica and thereafter allowed to cure. After curing, the transparent glove-like mold is separated from the replica.

In overmolding the painted prosthesis of either a human hand or foot, the distal digit portion of the transparent glove-like mold is filled at least in part with a viscous liquid of uncured silicone rubber material; the painted silicone rubber prosthesis is then inserted through the proximate end opening of the transparent glove-like mold. The glove is then stretched over the surface of the prosthesis such that the digits of the prosthesis fully extend into and are enclosed by the distal digit portion of the transparent glove-like mold. The overmold is positioned until its inner surface detail aligns substantially identically with the surface features of the silicone rubber prosthesis. Thereafter, radially compressive and proximately directed external force is sequentially applied beginning at the distal digit portion of the transparent glove-like mold to remove air bubbles and evenly distribute the uncured silicone rubber to a desired thickness over the painted surface of the prosthesis. The uncured silicone is then cured and the transparent glove-like mold removed from the silicone rubber prosthesis.

Although not shown in the drawings, the method of this invention would be substantially the same to overmold the painted prosthesis of a silicone rubber foot prosthesis. In this embodiment, the solid replica of the foot would be used to produce the mold of the monochromatic silicone rubber foot prosthesis. As in the method to overmold the human hand prosthesis, an elastomeric polymer coating material may be used to coat the replica to form the glove-like mold. The elastomeric polymer used to coat the replica would have the properties of transparency, of sufficient elasticity to permit the material to stretch tightly over the prosthesis, and of being non-adhesive to cured silicone rubber.

BRIEF DESCRIPTION OF THE DRAWINGS

These and other features and advantages will become appreciated as the same become better understood with reference to the following specification, claims, and drawings wherein:

DETAILED DESCRIPTION

In the process of overmolding a painted monochromatic silicone prosthesis to seal the painted surface beneath a clear coat of silicone rubber, a solid master model or solid replica of a human extremity is first molded utilizing well known techniques of the prior art.

Figure 1:
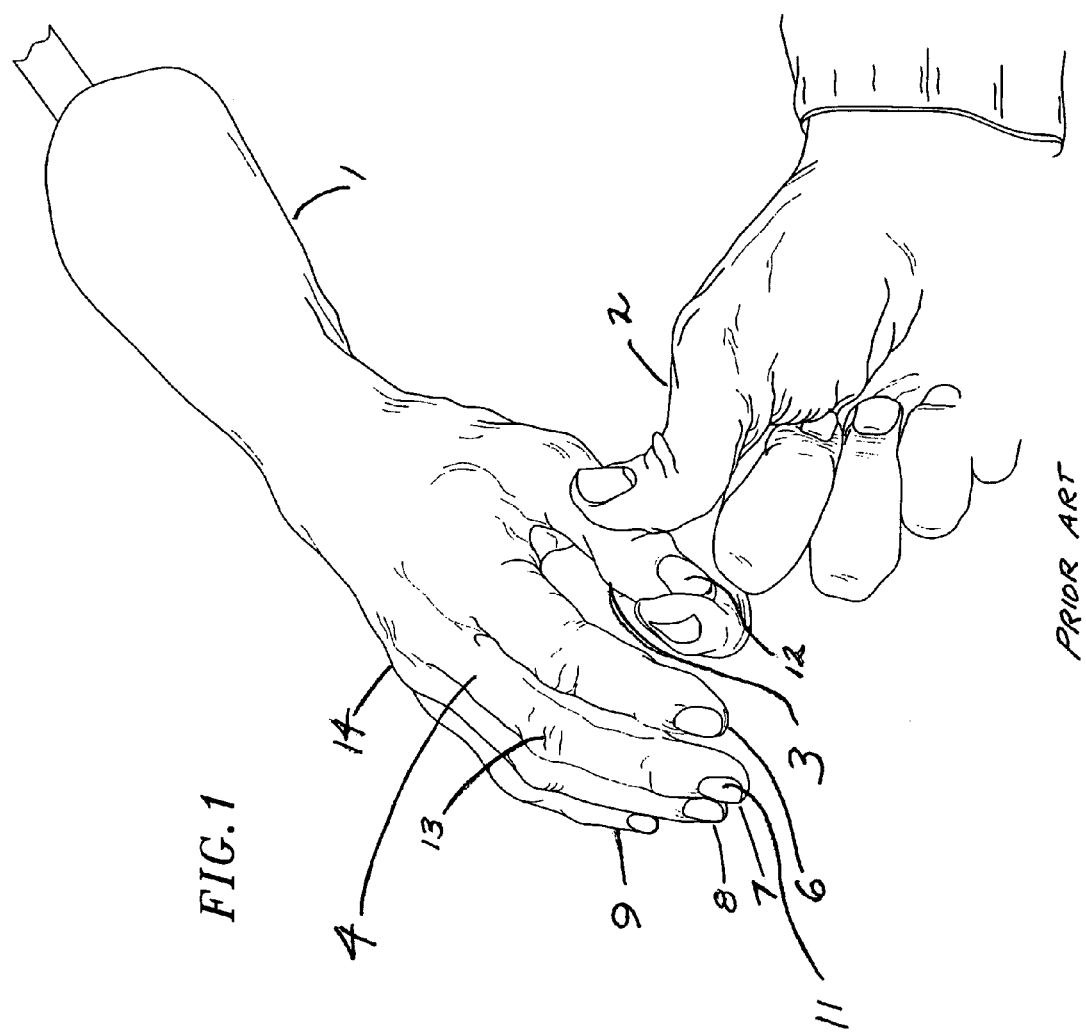
FIG. 1 is a perspective view illustrating a solid replica of a human extremity, namely, the human hand.

FIG. 1 is a perspective view of the solid replica 1 of the human hand from which the monochromatic silicone hand prosthesis is to be made. In FIG. 1, human hand 2 is illustrated placing pressure upon the thumb 3 of replica 1 to demonstrate the hardness of the master model, namely, the replica 1 of the hand. It can be seen in FIG. 1 that replica 1 has a distal digit portion 4 which contains thumb 3 and finger digits 6, 7, 8, and 9. The surface features of replica 1 such as fingernails 11, thumbnail 12, and the features of the skin covering the interphalangeal joints 13 and metacarpophlangeal joints 14 can also be seen in FIG. 1.

Figure 2:
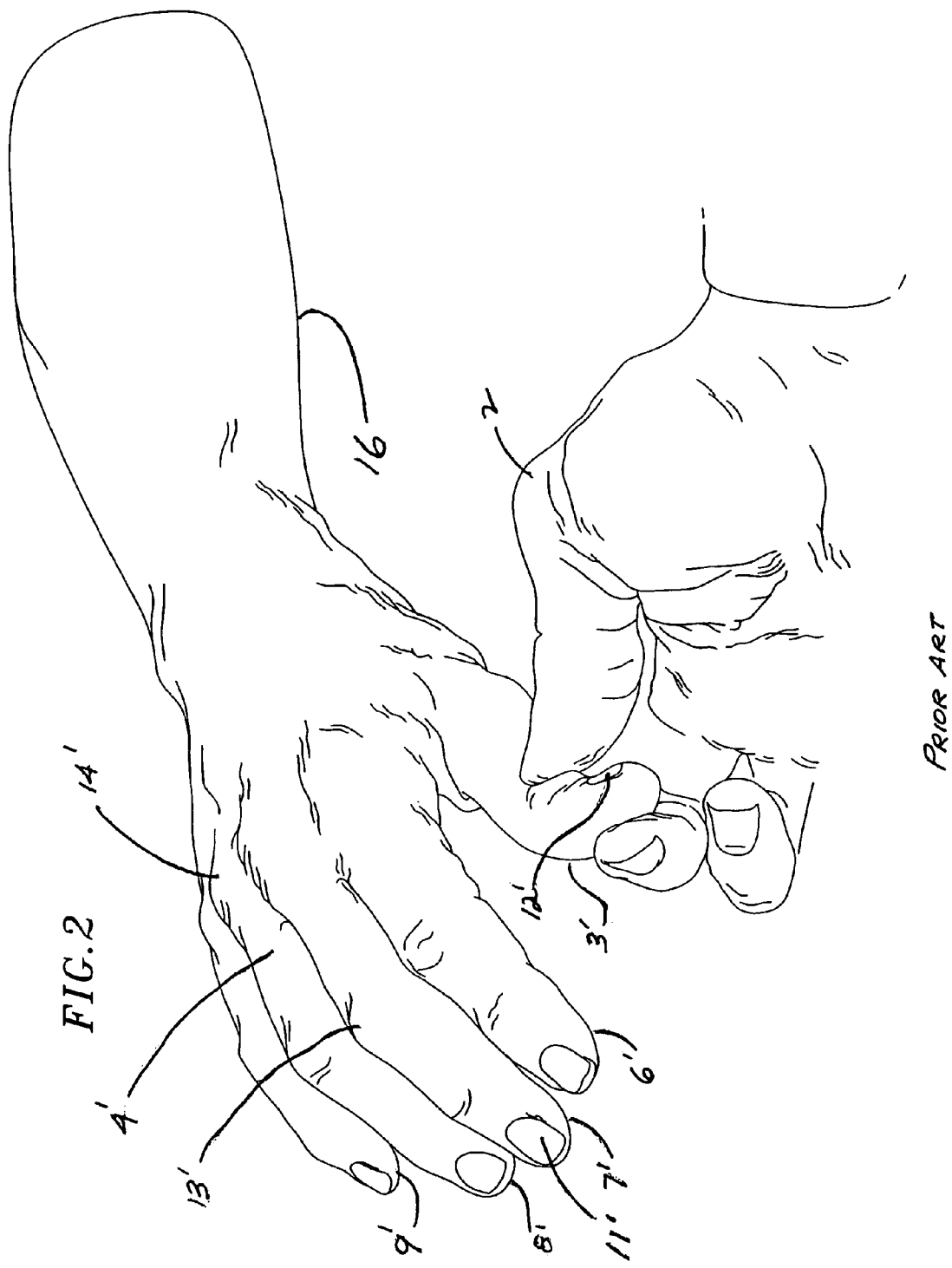
FIG. 2 is a perspective view of a monochromatic silicone hand prosthesis derived through conventional molding processes from the replica illustrated in FIG. 1.

Referring now to FIG. 2, a flexible monochromatic silicone rubber hand prosthesis 16 is illustrated that is derived from replica 1 using known prior art techniques. Human hand 2 is shown flexing thumb 3' to illustrate the flexibility of the silicone rubber hand prosthesis 16. As can further be seen in FIG. 2, silicone rubber hand prosthesis 16 has distal finger digits 6', 7', 8', and 9' that form, along with thumb 3', a distal portion 4' of the prosthesis. The skin surface features, that include fingernails 11', thumbnail 12', interphalangeal joints 13', and metacarpophalangeal joints 14', are shown in FIG. 2 and illustrated in the surface of silicone rubber hand prosthesis 16, and are painted or colored to closely resemble the skin tone and color of the human hand. Although not shown in the drawings, a silicone rubber foot prosthesis may be made from a replica where the toe digits would be integrable with the distal portion of the foot prosthesis. And in the same way, other prostheses of human extremities may be made utilizing known techniques of the prior art.

In the method of this invention, a transparent glove-like overmold is made from replica 1 by dipping replica 1 in an elastomeric polymer material to form a coating of desired thickness where the elastomeric polymer material has the property of being elastic, transparent, and non-adhesive to cured silicone rubber. The elastomeric polymer material may also be applied by spraying or brushing the material onto the replica until the desired thickness of the glove-like overmold has been achieved. The preferred material in the method of this invention is a thermoplastic elastomer material having the above recited properties, namely, elasticity, transparency, and non-adhesiveness to silicone rubber. Any moldable material having these same properties as, for example, a polyurethane elastomer may also be used to form the transparent glove-like overmold to overmold the painted surface of the silicone rubber hand prosthesis.

Figure 3:
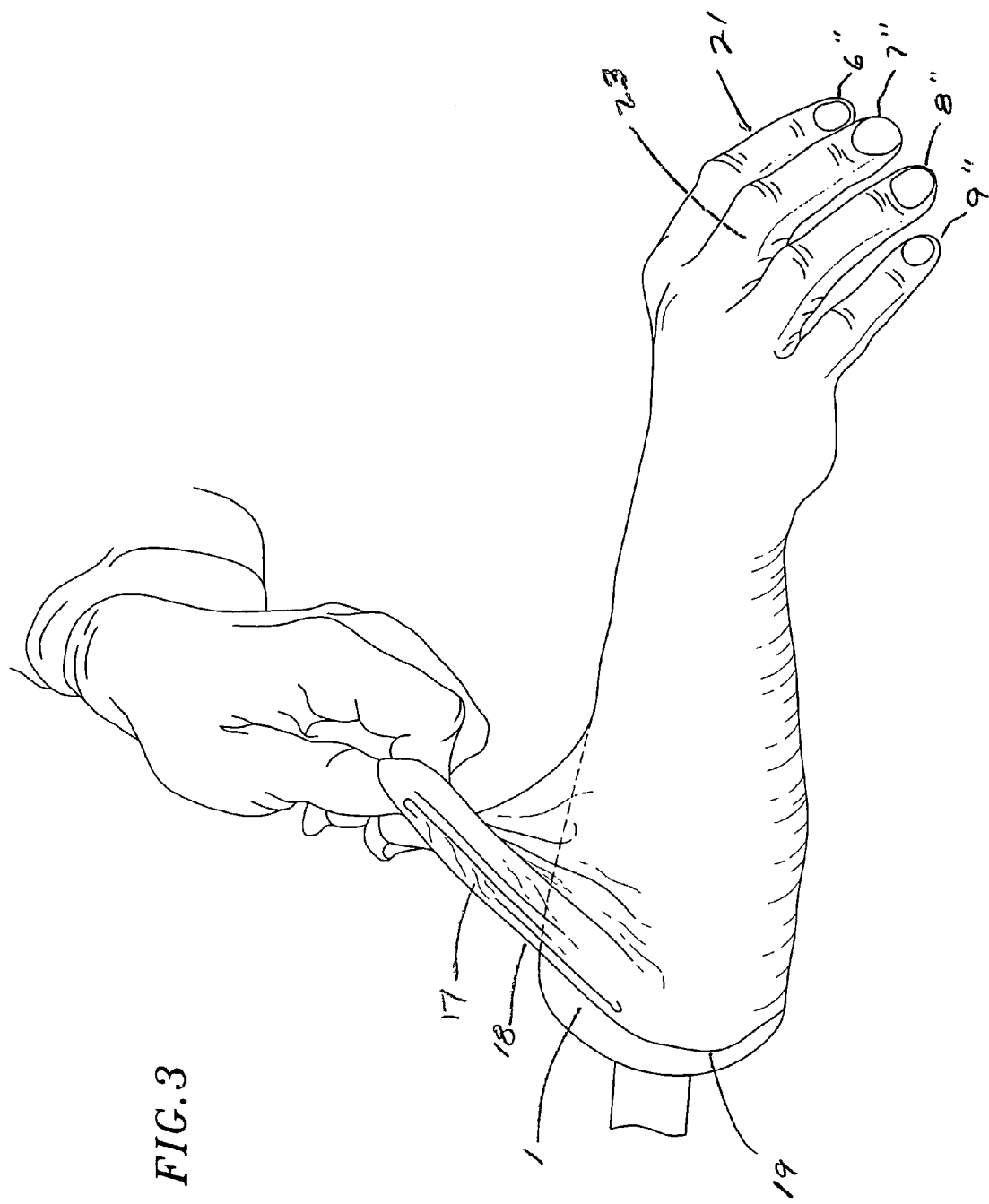
FIG. 3 is a perspective view of the transparent glove overmold of this invention illustrating the elastic flexibility and transparent property of the elastomeric polymer material of which the transparent glove is constructed.
Figure 4:
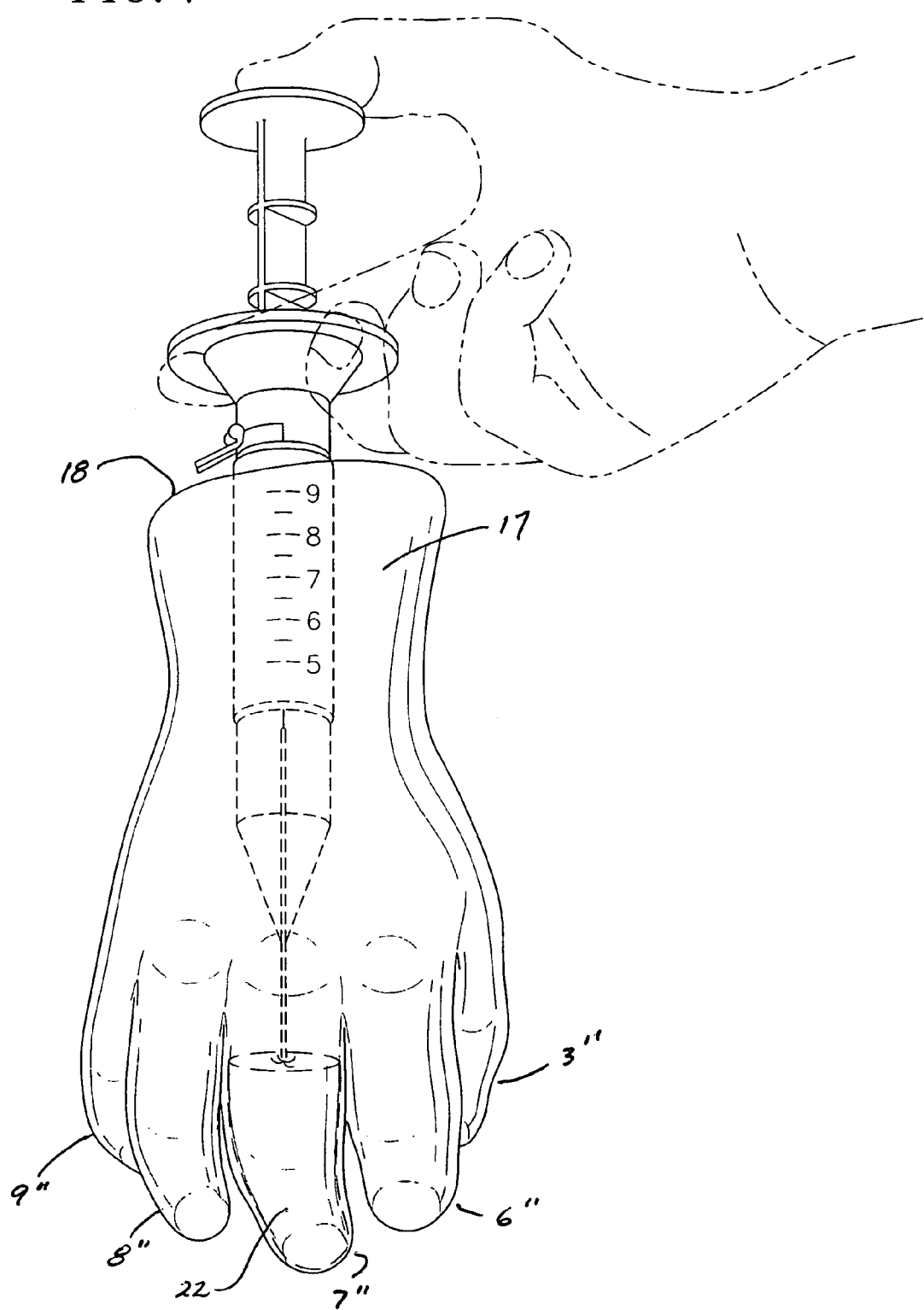
FIG. 4 illustrates the step in the method of this invention where the distal digits of the transparent glove, after the glove is separated from the replica, are at least in part filled with a viscous uncured silicone liquid.

As can be seen in FIG. 3, transparent glove-like overmold 17 completely and integrally encloses replica 1 but has an opening 18 at proximate end 19. Opening 18 at proximate end 19 of the glove, permits silicone prosthesis 16 to be inserted into glove 17 as part of the overmolding process. The material properties of the glove that include elasticity and transparency are demonstrated in FIG. 3. At the distal end 21 of transparent glove 17, the glove has corresponding finger digits 6", 7", 8", and 9" covering finger digits 6, 7, 8 and 9 of replica 1 which are substantially identical and like dimensioned as shown in FIG. 3 and FIG. 4 at distal digit portion 23 of the glove. As can further be seen in FIG. 3, transparent glove-like overmold 17 has an inner surface, a distal portion containing finger digits 6",7", 8", and 9", a proximate portion at proximate end 19, and an intermediate portion therebetween.

After transparent glove 17 is removed from replica 1, distal finger digits 6", 7", 8", and 9" and thumb 3" are filled in part with a predetermined quantity of a viscous uncured silicone liquid 22 as shown in FIG. 4. Although implied, but not shown in the drawings, each of the distal digits and thumb of the transparent glove-like overmold are at least in part filled as illustrated in FIG. 4 with liquid 22. The liquid silicone rubber material 22 is preferably a highly adhesive silicone such as RTV silicone (room temperature vulcanizing), or a tin cure silicone, or an additive cure platinum based catalyst silicone, or a condensation curing silicone.

Figure 5:
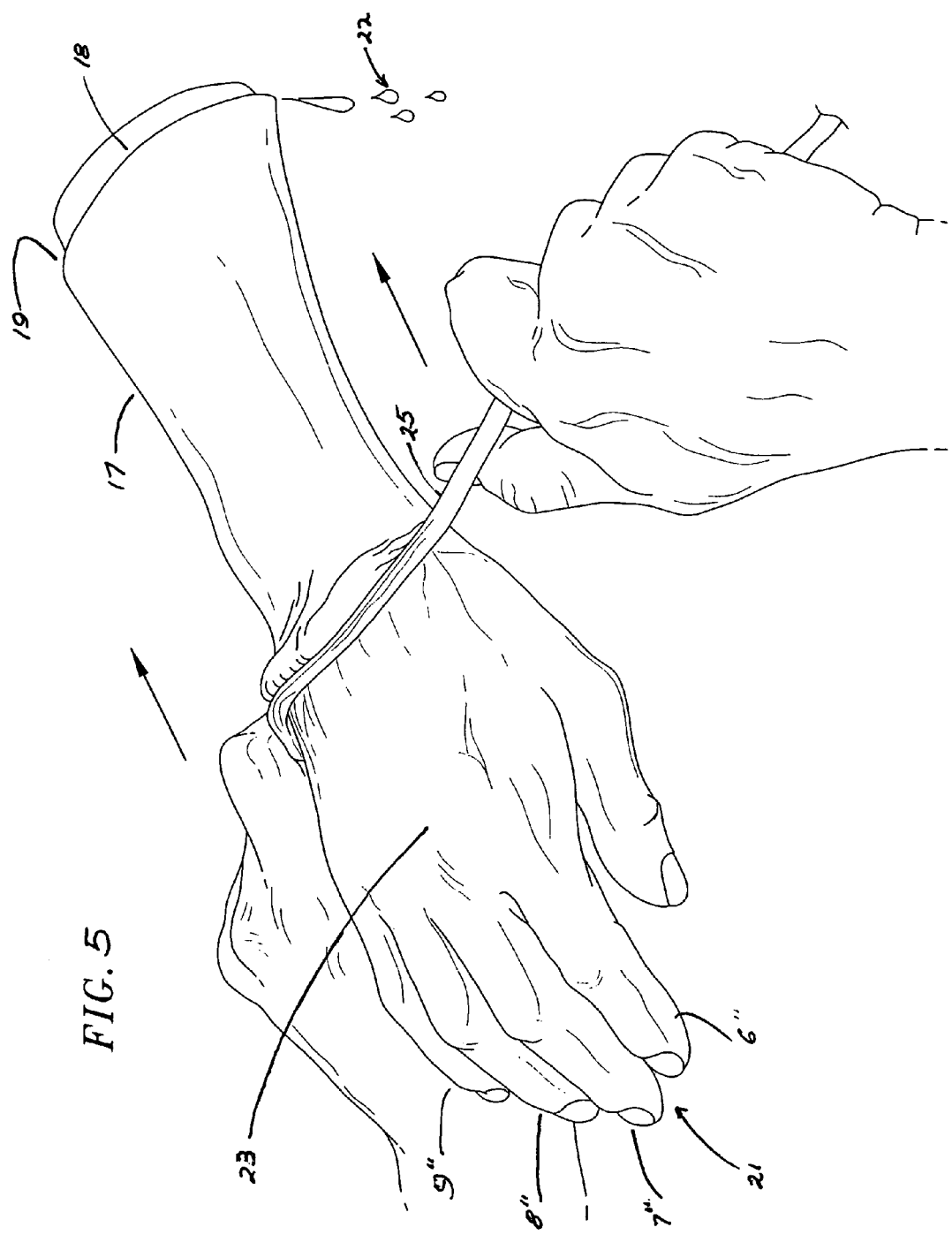
FIG. 5 illustrates the step in the method of this invention, after the painted monochromatic silicone hand prosthesis is fully inserted into the transparent glove and the glove is stretched over the surface of the prosthesis, that external force is applied radially compressively in a proximate direction to distribute the viscous uncured silicone liquid uniformly over the surface of the hand prosthesis.

The overmolding step of the method of this invention is illustrated in FIG. 5. As can be seen in FIG. 5, the painted silicone rubber prosthesis 16 is inserted though opening 18 of proximate end 19 of the transparent glove. Transparent glove 17 is then stretched tightly over the surface of prosthesis 16 such that distal finger digits 6', 7', 8', and 9' and thumb 3' of prosthesis 16 are enveloped and are enclosed by corresponding finger digits at distal digit portion 23 of transparent glove 17. After glove 17 is stretched over the surface of prosthesis 16, an external compressive force is applied in a radially inward compressive and proximal direction by vinyl hose 25 forcing the viscous uncured silicone liquid 22 to be distributed uniformly over the surface of prosthesis 16. As illustrated in FIG. 5, excess silicone liquid 22 is radially compressed sequentially in a proximate direction toward opening 18 through which the silicone liquid 22 is permitted to escape along with air bubbles that have formed in the liquid. By successive application of external force through vinyl hose 25, silicone liquid is distributed uniformly over the surface of prosthesis 16 and the air bubbles released through proximate opening 18 of the glove.

Since the elastomeric polymer material of which transparent glove 17 is constructed has the property, in addition to being elastic and transparent, of being non-adhesive to cured silicone rubber, silicone liquid 22 upon curing will bond to the painted silicone surface of prosthesis 16 but not to transparent glove 17. Thus, upon silicone liquid 22 curing, transparent glove 17 may be removed from prosthesis 16 without distortion of or otherwise impairing the painted surface of prosthesis 16.

While I have shown and described the method of overmolding the painted surface of a monochromatic silicone hand prosthesis to protect the painted surface from abrasions while preserving the aesthetic and realistic appearance of the human hand, it is to be understood that the invention is subject to many modifications without departing from the scope and spirit of the claims as recited.

What is claimed is:

1. A method for overmolding a silicone rubber prosthesis of a human extremity, said silicone rubber prosthesis of the type where the silicone rubber prosthesis is molded from a replica made of said human extremity, said silicone rubber prosthesis having a distal end, a proximate end, comprising,
    (a) painting said surface features of said silicone rubber prosthesis;
    (b) forming a transparent glove-like overmold of desired thickness of said replica, said glove-like overmold having an inner surface and outer surface where said inner surface has surface features substantially identical to said replica and where said transparent glove-like overmold has a distal portion, an intermediate portion, and a proximate portion, said proximate portion having an opening therein sufficiently dimensioned to permit said transparent glove-like overmold to receive said painted surface of said silicone rubber prosthesis, and where said transparent glove like overmold is made of an elastomeric polymer material having the property of being non-adhesive to cured silicone rubber and transparent;
    (c) after step (b), filling said distal portion of said transparent glove-like overmold at least in part with a viscous uncured silicone rubber material;
    (d) after step (c), inserting said silicone rubber prosthesis into said opening such that each said distal end of said silicone rubber prosthesis is enclosed by said distal portion of said transparent glove-like overmold;
    (e) after step (d), stretching said inner surface of said transparent glove-like overmold over said painted surface features and aligning said inner surface features with said painted surface features and then applying an external force to said transparent glove-like overmold so as to distribute said viscous uncured silicone material uniformly over said painted surface; and
    (f) after step (e), curing said viscous uncured silicone rubber material and removing said transparent glove-like overmold from said silicone rubber prosthesis.

2. The method recited in claim 1 where said silicone rubber prosthesis of said human extremity is a silicone rubber hand prosthesis.

3. The method recited in claim 1 where said silicone rubber prosthesis of said human extremity is a silicone rubber foot prosthesis.

4. The method recited in claim 1 wherein said elastomeric polymer material is a thermoplastic elastomer.

5. The method recited in claim 1 wherein said elastomeric polymer material is a polyurethane elastomer.

6. The method recited in claim 1 further comprising after step (e), the step of curing said uncured viscous silicone rubber material.

7. The method recited in claim 6 wherein said elastomeric polymer material is a thermoplastic elastomer.

8. The method recited in claim 6 wherein said elastomeric polymer material is a polyurethane elastomer.

9. In a method for overmolding the geographic surface features of a silicone rubber prosthesis of a human extremity, said silicone rubber prosthesis of the type where the silicone rubber prosthesis is molded from a replica made of said human extremity, where said replica has a distal end surface, an intermediate surface portion, and a proximate end surface substantially identical respectively to the distal portion, intermediate portion, and proximal portion of said silicone rubber prosthesis and where said silicone rubber prosthesis has a painted surface, the improvement comprising the steps of:
    (a) applying an elastomeric polymer material having the property of being transparent and non adhesive to cured silicone rubber to said replica to form a transparent glove-like overmold of desired thickness, said transparent glove-like overmold having an inner surface and outer surface where said inner surface has surface features substantially identical to the surface features of said replica;
    (b) separating said transparent glove-like overmold from said replica where said inner surface features of said transparent glove-like overmold are substantially identical respectively to said distal end surface of said replica, said intermediate surface portion of said replica, and said proximate end surface of said replica;
    (c) after step (b), filling said transparent glove-like overmold at least in part with a viscous uncured silicone rubber material;
    (d) after step (c) inserting said painted silicone rubber prosthesis into said transparent glove-like overmold sufficiently such that said silicone rubber prosthesis extends into said transparent glove-like overmold and where said inner surface of said transparent glove-like overmold and said painted surface of said silicone rubber prosthesis are oppositely disposed in mirror image relationship;
    (e) after step (d) stretching said inner surface of said transparent glove-like overmold over and into alignment with said painted surface features of said silicone rubber prosthesis and then applying an external force to said transparent glove-like overmold so as to distribute said viscous uncured silicone material uniformly over said painted surface of said silicone rubber prosthesis; and
    (f) after step (e), curing said viscous uncured silicone rubber material and removing said transparent glove-like overmold from said silicone rubber prosthesis.

10. The method recited in claim 9 where said silicone rubber prosthesis of a human extremity is a silicone rubber hand prosthesis.

11. The method recited in claim 9 where said silicone rubber prosthesis of a human extremity is a silicone rubber foot prosthesis.

12. The method recited in claim 9 wherein said elastomeric polymer material is a thermoplastic elastomer.

13. The method recited in claim 9 wherein said elastomeric polymer material is a polyurethane elastomer.

14. The method recited in claim 9 further comprising after step (d), the step of curing said uncured viscous silicone rubber material and removing said transparent glove-like overmold from said silicone rubber prosthesis.

15. The method recited in claim 14 wherein said elastomeric polymer material is a thermoplastic elastomer.

16. The method recited in claim 14 wherein said elastomeric polymer material is a polyurethane elastomer.

17. The method recited in claim 9 wherein said elastomeric polymer material is applied to said replica by dipping said replica in said elastomeric polymer material.

18. The method recited in claim 9 wherein said elastomeric polymer material is applied to said replica by spraying said replica with said elastomeric polymer material.

19. The method recited in claim 9 wherein said elastomeric polymer material is applied to said replica by brushing said elastomeric polymer material onto said replica.

* * * * *